United States Patent
Hagglund et al.

(10) Patent No.: US 10,244,729 B2
(45) Date of Patent: Apr. 2, 2019

(54) MILK SAMPLING DEVICE

(71) Applicant: DELAVAL HOLDING AB, Tumba (SE)

(72) Inventors: Christoffer Hagglund, Tumba (SE); Gunvor Nilsson, Tumba (SE); Torbjorn Petterson, Tumba (SE)

(73) Assignee: DELAVAL HOLDING AB, Tumba (SE)

( * ) Notice: Subject to any disclaimer, the term of this patent is extended or adjusted under 35 U.S.C. 154(b) by 346 days.

(21) Appl. No.: 15/306,143

(22) PCT Filed: Apr. 27, 2015

(86) PCT No.: PCT/SE2015/050465
§ 371 (c)(1),
(2) Date: Oct. 24, 2016

(87) PCT Pub. No.: WO2015/167391
PCT Pub. Date: Nov. 5, 2015

(65) Prior Publication Data
US 2017/0042111 A1    Feb. 16, 2017

(30) Foreign Application Priority Data
Apr. 30, 2014 (SE) ...................................... 1450514

(51) Int. Cl.
*G01N 1/00* (2006.01)
*A01J 5/04* (2006.01)
(Continued)

(52) U.S. Cl.
CPC .................. *A01J 5/045* (2013.01); *A01J 5/01* (2013.01); *G01N 1/00* (2013.01); *G01N 1/18* (2013.01); *G01N 33/04* (2013.01)

(58) Field of Classification Search
CPC .. G01N 33/04; G01N 1/2035; G01N 21/3577; G01N 33/06; G01N 33/54386;
(Continued)

(56) References Cited

U.S. PATENT DOCUMENTS

| 3,085,425 A | * | 4/1963 | Roman | ............... | G01N 15/0618 |
| | | | | | 73/61.71 |
| 5,746,153 A | * | 5/1998 | Hoefelmayr | ............ | A01J 5/045 |
| | | | | | 119/14.01 |

(Continued)

FOREIGN PATENT DOCUMENTS

| CA | 2 424 629 A1 | 10/2004 |
| DE | 34 33 865 A1 | 3/1986 |

(Continued)

OTHER PUBLICATIONS

International-Type Search Report, dated Dec. 30, 2014, from corresponding PCT application.
(Continued)

*Primary Examiner* — Andre J Allen
(74) *Attorney, Agent, or Firm* — Young & Thompson

(57) ABSTRACT

A milk sampling device includes a housing forming an inner space, an inlet opening to the inner space, a deflector member with an upper surface mounted in the inner space of the housing in a position vertically below the inlet opening, a flow passage formed between a periphery edge portion of the deflector member and an inner surface of the housing, and a milk sampling passage provided with an opening which constitutes a part of the flow passage. The upper surface of the deflector member comprises a plurality of a upwardly extending members arranged at a distance from each other in the vicinity of the periphery edge portion of the deflector member such that flow channels are formed between adjacent upwardly extending members.

21 Claims, 2 Drawing Sheets

(51) Int. Cl.
G01N 1/18 (2006.01)
A01J 5/01 (2006.01)
G01N 33/04 (2006.01)

(58) Field of Classification Search
CPC .... G01N 33/6893; G01N 21/78; G01N 21/82; G01N 2469/20; G01N 33/487; G01N 33/54373; G01N 33/5695; G01N 15/06; G01N 1/18; G01N 2015/0065; G01N 2015/0693; G01N 21/05; G01N 21/6428; G01N 2800/365; G01N 33/48; G01N 33/5304; G01N 33/6854; G01N 15/042; G01N 2021/0325; G01N 21/0332; G01N 21/359; G01N 21/49; G01N 21/6486; G01N 2333/245; G01N 2333/495; G01N 33/5005; G01N 33/5091; G01N 33/54306; G01N 33/56938; G01N 33/6803; G01N 33/689; G01N 33/74; G01N 33/86; G01N 15/10; G01N 15/1031; G01N 15/1056; G01N 1/10; G01N 1/38; G01N 1/4077; G01N 2001/205; G01N 2001/2071; G01N 2011/008; G01N 2013/003; G01N 2015/008; G01N 2015/1062; G01N 2021/3137; G01N 2021/3174; G01N 2021/3595; G01N 2021/4707; G01N 2021/6421; G01N 2030/8836; G01N 21/253; G01N 21/278; G01N 21/31; G01N 21/51; G01N 21/59; G01N 21/64; G01N 21/80; G01N 2201/0484; G01N 2201/0612; G01N 2201/102; G01N 2201/1293; G01N 2333/183; G01N 2333/30; G01N 2333/31; G01N 2333/4713; G01N 2333/4715; G01N 2333/485; G01N 2333/70535; G01N 2333/72; G01N 2333/79; G01N 2333/952; G01N 2400/00; G01N 2400/02; G01N 27/026; G01N 27/06; G01N 27/622; G01N 2800/368; G01N 2800/7095; G01N 31/221; G01N 33/14; G01N 33/48735; G01N 33/48785; G01N 33/49; G01N 33/493; G01N 33/5047; G01N 33/52; G01N 33/525; G01N 33/5308; G01N 33/54366; G01N 33/552; G01N 33/558; G01N 33/56911; G01N 33/56983; G01N 33/57415; G01N 33/57488; G01N 33/582; G01N 33/62; G01N 33/6872; G01N 33/743; G01N 33/94; G01N 33/9446; G01N 33/946; G01N 35/109; G01N 35/1095; G01N 35/1097

See application file for complete search history.

(56) References Cited

U.S. PATENT DOCUMENTS

| | | | |
|---|---|---|---|
| 2003/0077203 A1* | 4/2003 | Gudmundsson | A01J 5/045 119/14.18 |
| 2003/0143748 A1* | 7/2003 | Gudmundsson | A01J 5/045 119/14.02 |
| 2003/0143749 A1* | 7/2003 | Gudmundsson | A01J 5/045 119/14.18 |
| 2007/0113790 A1* | 5/2007 | Akerman | A01J 5/0134 119/14.02 |
| 2009/0251683 A1* | 10/2009 | Wardlaw | G01N 33/54373 356/39 |
| 2010/0071626 A1 | 3/2010 | Hoey | |
| 2011/0120378 A1 | 5/2011 | Johannesson | |
| 2012/0160174 A1* | 6/2012 | Gudmundsson | A01J 5/045 119/14.02 |

FOREIGN PATENT DOCUMENTS

| | | |
|---|---|---|
| EP | 1 254 595 A2 | 11/2002 |
| EP | 1 443 324 A1 | 8/2004 |
| SU | 438397 A1 | 1/1975 |
| SU | 1236214 A1 | 6/1986 |
| SU | 1335210 A1 | 9/1987 |
| SU | 1479031 A1 | 5/1989 |
| SU | 1544307 A1 | 2/1990 |
| WO | 2005/020674 A1 | 3/2005 |
| WO | 2012/152441 A1 | 11/2012 |

OTHER PUBLICATIONS

International Search Report, dated Aug. 20, 2015, from corresponding PCT application.
Supplementary International Search Report, dated Aug. 26, 2016, from corresponding PCT application.

\* cited by examiner

MILK SAMPLING DEVICE

THE BACKGROUND OF THE INVENTION AND PRIOR ART

The present invention relates to a milk sampling device comprising a housing forming an inner space, an inlet opening to the inner space, a deflector member provided with an upper surface mounted in the inner space of the housing in a position below the inlet opening where it is configured to receive and temporarily accumulate milk entering the housing through the inlet opening, a flow passage formed between a periphery edge portion of the deflector member and an inner surface of the housing, and a milk sampling passage provided with at least one opening which constitutes a part of the flow passage.

Such a milk sampling device may be used to take milk samples of the milk flow in a milk line. The milk entering the milk sampling device hits the upper surface of the deflector member before it is directed radially outwardly towards a surrounding flow passage. A smaller part of the milk flow through the flow passage is guided into the opening of the milk sampling passage from which it is conducted to a milk sampling container such as a test tube or the like. The milk sampling device can be arranged into or in the vicinity of a milk meter in a milking stall.

The milk flow from an animal varies during a milking process. The content of substances such as fats, proteins, lactose, minerals etc. in the milk is not constant during a milking process. It has been verified by experiment that milk sampling devices of the initially mentioned kind discharge a higher percentage of milk to a milk sample at high milk flows than at low milk flows. In view of this fact, the milk sample will not always be representative with a desired accuracy for the whole quantity of milk obtained during a milking process.

SUMMARY OF THE INVENTION

The object of the present invention is to provide a milk sampling device of the initially mentioned kind by which it is possible to take a representative milk sample from a milking process with a variable milk flow and a milk sampling device which not need to be arranged in a very accurate mounting position.

These objects are achieved by the initially mentioned milk sampling device, which is characterized in that the upper surface of the deflector member comprises a plurality of upwardly extending members arranged at a distance from each other in the vicinity of the periphery edge portion of the deflector member such that flow channels are formed between adjacent upwardly extending members. The upper surface of the deflector member has a shape such that an amount of milk accumulates on the surface during a milking process. When the milk flow from the inlet opening hits the accumulated milk on the upper surface of the deflector member, the accumulated milk is pressed outwardly towards a periphery portion of the deflector member. Thus, a milk flow is achieved on the upper surface of the deflector member towards its peripheral portion. The upwardly extending members reduce the flow area of the milk flow at the periphery portion of the upper surface of the deflector member.

The reduced flow area at the periphery portion of the upper surface results in a raised milk level in at least the flow channels between the upright standing members. Consequently, the milk will leave the upper surface of the deflector member in the form of a predetermined number of milk streams in predetermined directions. With such a controlled milk flow from the deflector member to the flow passage, it is possible to discharge a substantially equal percentage of the milk to the sampling passage at variable milk flows during a milking process of an animal. Furthermore, it is possible to produce a substantially uniform milk flow through all flow channels even when the upper surface of the deflector member is arranged in a somewhat inclined position. Consequently, the deflector member does not need to be mounted in a completely accurate mounting position.

According to an embodiment of the invention, said upwardly extending members are arranged along a circular path at equal distances from each other. In this case, the upwardly extending members provide intermediate flow channels of the same size and with regular intervals along the whole periphery of the upper surface. Such flow channels spread the milk substantially uniformly to the flow passage.

According to an embodiment of the invention, the number of upwardly extending members are in the range of 10-20. It has been verified by experiment that about 15 upwardly extending members equally arranged around the periphery of the upper surface of the deflector member provide a very uniform milk flow to the flow passage. The number of flow channels, which are formed between adjacent upwardly extending members, are the same as the numbers of upwardly extending members. The width of the upwardly extending members defines the width of the flow channels. The width of the upwardly extending members may be equal or smaller than the width of the flow channels. Alternatively, the width of the upwardly extending members is larger than the width of flow channels. All upwardly extending members may be of equal size. Alternatively, the height and/or the width of the upwardly extending members may vary. The width of an upwardly extending member may be constant or varying along its height.

According to an embodiment of the invention, the upper surface of the deflector member has a concave shape. In this case, the upper surface is bowl-shaped and the peripheral edge portion of quantity of milk may be accumulated on such an upper surface of a deflector member.

According to an embodiment of the invention, the opening of the sampling passage occupies an area in the range of 1-5 percent of the flow passage. In this case, about 1-5 percent of the milk in the flow passage is discharged via the opening to the milk sampling passage. Preferably, the opening occupies an area of about 2-3% of the flow passage. In case the flow passage is annular, the opening of the sampling device may occupy about 10 degrees of the flow passage. The discharged amount of milk to the milk sampling passage should be small but large enough to constitute a representative milk sample of the milk from a milking process. It is possible to provide the milk sampling device with more than one opening to the milk sampling passage. In this case, the openings may be arranged at constant intervals along the flow passage. Two such openings may, for example, be arranged at opposite sides of the flow passage. The use of several openings to the milk sampling passage, makes the milk sampling device even less sensitive for inclination.

According to an embodiment of the invention, the upper surface of the deflector member is larger than the cross section area of the inlet opening. Thereby, all milk entering the milk sampling device hits the upper surface of the deflector member when it falls vertically downward from the inlet opening to the deflector member. The deflector member may be arranged in a position in relation to the inlet opening such that a vertical axis extends both through a center position of the inlet opening and a center position of the upper surface of the deflector member. In this case, the milk hits a center area of the upper surface of the deflector member. Preferably, the upper surface of the deflector member is at least twice as large as the cross section area of the inlet opening.

According to an embodiment of the invention, it comprises at least one support member configured to support the deflector member in said vertical position below the inlet opening. Preferably, several support members are used which are arranged at a distance from each other such that they accomplish a stable support of the deflector member in the housing.

According to an embodiment of the invention, it comprises a locking member configured to lock the deflector member in a specific angular position in which it delivers milk to the opening of the milk sampling passage via one predetermined flow channel located between two adjacent upwardly extending members. In order to avoid that an upwardly extending member more or less blocks the milk flow to the opening of the sampling passage, it is suitable to arrange the deflector member in an angular position in which the milk flow in one of the flow channels is used to direct milk to the opening of the sampling passage. The milk flow in the remaining flow channels are directed to the remaining area of the flow passage. In this case, the width of the predetermined flow channel may correspond to the width of the opening to the milk sampling passage.

According to an embodiment of the invention, it comprises a support member having also the task to define the opening of the milk sampling passage. In this case, the walls forming the opening to the sampling passage has a shape such that they also form a support area of the deflector member. Thereby, the construction of the sampling device will be further simplified.

According to an embodiment of the invention, the housing comprises an upper housing member and a lower housing member. The upper housing member and the lower housing member may be substantially bowl-shaped. In this case, the upper housing member forms an upper portion of the inner space of the housing and the lower housing forms a lower portion of the inner space of the housing. The upper housing member may comprise a connection portion and the lower housing member may comprise a connection portion by which the housing members are releasably connectable to each other. By means of such connection portions, it is easy to connect the housing members and disconnect them from each other.

According to an embodiment of the invention, the upper housing member comprises an inlet nipple to be connected to a milk tube. It is uncomplicated to connect and disconnect a milk tube to a nipple. The milk tube may conduct milk from one teat cup. In this case, it is possible to take a milk sample from one teat of an animal during a milking process. Alternatively, the milk tube receives milk from several teat cups. In this case, a milk sample is taken from several teats of an animal during a milking process.

According to an embodiment of the invention, the lower housing member comprises an outlet nipple through which milk is conducted to a milk sampling container. Such a nipple may be connected to a milk tube conducting milk to a milk sampling container which may be a test tube.

According to an embodiment of the invention, the lower housing member comprises an outlet nipple through which milk is conducted to a milk meter. In this case, the milk meter measures the milk flow in a position immediately downstream of the milk sampling device. Since the milk sampling device discharges the same percentage of the milk flow to the sampling passage at all possible milk flows during the whole milk process, it is able to provide a representative milk sample from a milking process regardless of the milk flow variations during the milking process. Thus, the milk sampling device does not need to receive information about the current milk flow from a milk meter in order to provide a representative milk sample from a milking independently of a milk meter and it may be given a very simple design.

According to an embodiment of the invention at least one of the housing members comprises a sealing member performing a sealed connection between the housing members in a connected state. Thereby, leakage between the housing members is avoided.

According to an embodiment of the invention, the milk sampling device comprises no more than three separate components namely the upper housing member, the lower housing member and the deflector member. It is to be noted that a sealing member may be needed between the upper housing member and the lower housing member. The sealing member may be co-moulded to one of the upper housing member or lower housing member or be a separate part. In the latter case the sealing member is not to be regarded as a component. Said components may be formed by a suitable plastic material. Such components of the milk sampling device can be manufactured to a very low cost. Furthermore, the milk sampling device includes no movable parts which ensures a long and reliable function.

BRIEF DESCRIPTION OF THE DRAWINGS

The present invention is now to be explained more closely by means of a preferred embodiment which is disclosed as an example and with reference to the attached drawings.

BRIEF DESCRIPTION OF A PREFERRED EMBODIMENT OF THE INVENTION

Figure 1:
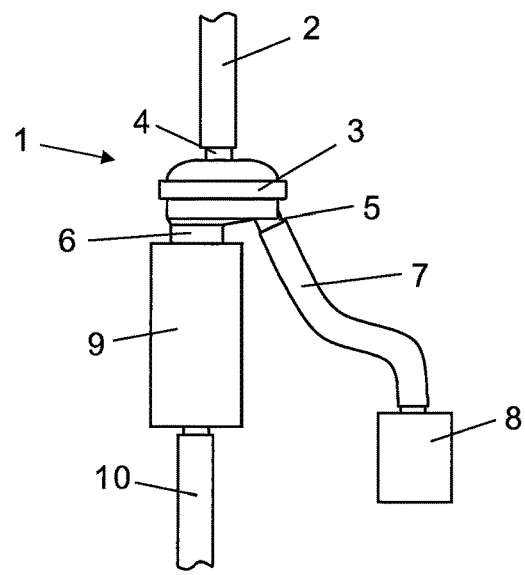
FIG. 1 shows a milk sampling device, according to the invention, in a mounted state in a milk line.

FIG. 1 shows a milk sampling device 1 mounted in a milk line which conduct milk from an animal during a milking process. The milk line comprises a milk tube 2 conducting milk from one or several teats of an animal. The milk sampling device comprises a housing 3. The housing 3 is, at an upper portion, provided with an inlet nipple 4 to be connected to the milk tube 2. The housing 3 comprises a first outlet nipple 5 to be connected to a milk sampling tube 7 conducting milk to a milk sample container 8. The housing 3 comprises a second outlet nipple 6 to be connected to a milk meter 9 configured to measure the milk flow in the milk line. The milk meter 9 is connected to an outlet milk tube 10 conducting the milk to a not shown milk tank which may be an end unit. The milk sampling device 1 is constructed by no more than three separate components.

Figure 2:
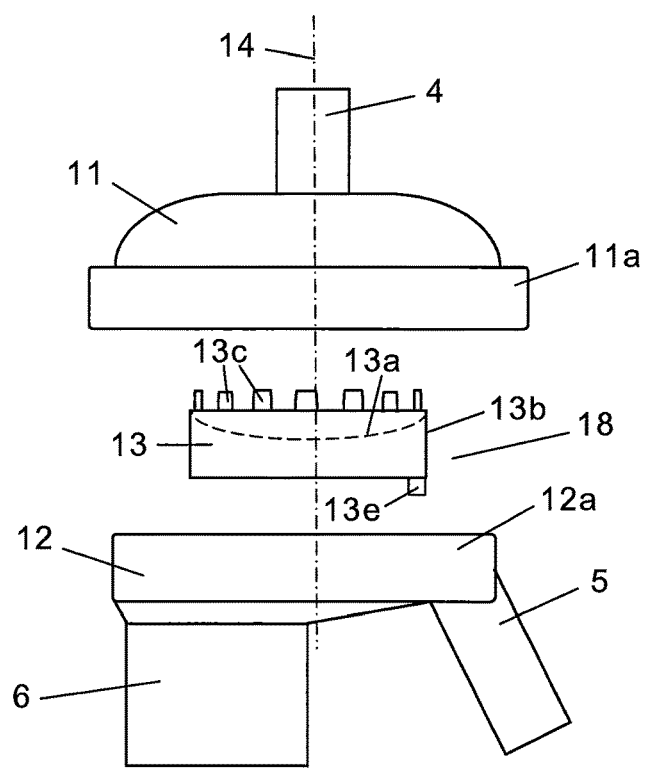
FIG. 2 shows the including components of the milk sampling device in a disassembled state.

FIG. 2 shows the three components of the milk sampling device 1 in a disassembled state. The milk sampling device 1 comprises a first component in the form of a substantially bowl-shaped upper housing member 11. The inlet nipple 4 is arranged in a central position on the top of the upper housing member 11. The upper housing member 11 comprises, at a lower part, a connection portion 11a. The milk sampling device 1 comprises a second component in the form of a substantially bowl-shaped lower housing member 12. The first outlet nipple 5 is arranged at a peripheral part of the lower housing member 12. The second outlet nipple 6 is arranged at a bottom part of the lower housing member 12. The lower housing member 12 comprises, at an upper part, a connection portion 12a. The milk sampling device 1 comprises a third component in the form of a deflector member 13. The deflector member is configured to be mounted inside an inner space of the housing 3 which is formed by the two bowl-shaped housing members 11, 12 in a connected state. The three components 11, 12, 13 can be manufactured by a suitable plastic material. A vertical central axis 14 through the units 11, 12, 13 is indicated.

Figure 3:
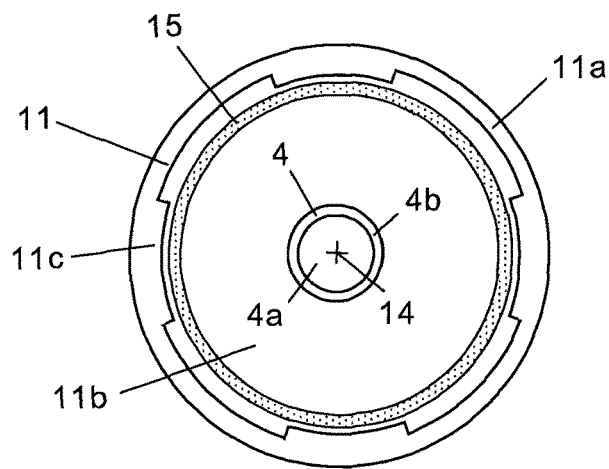
FIG. 3 shows a view of the upper housing member in FIG. 2 from the below.

FIG. 3 shows the upper housing member 11 in a view from below. The inlet nipple 4 comprises an inlet opening 4a to the inner space of the housing 3. The vertical central axis 14 extends centrally through the inlet opening 4a. The inlet nipple 4 is provided with a downwardly directed edge portion 4b which extends around the inlet opening 4a. The object of the edge portion 4b is to ensure that the milk falls vertically downwards in the inner space of the housing 3. Thus, the edge portion 4b prevents that the milk flows along the inner surface 11b of the upper housing member 11. The connection portion 11a comprises an internally arranged circular sealing member 15. The connection portion 11a also comprises a number of radial portions 11c arranged at constant intervals around a periphery portion of the connection portion 11a. The radial portions 11c extend radially inwardly from the inner surface 11b of the upper housing member 11.

Figure 4:
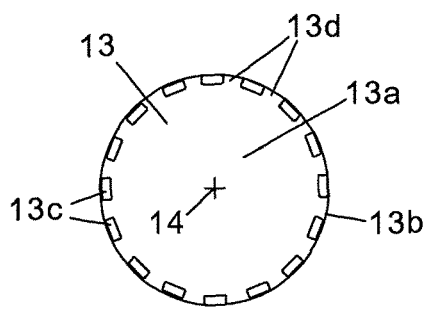
FIG. 4 shows a view of the deflector member in FIG. 2 from the above and FIG. 5 shows a view of the lower housing member in FIG. 2 from the above.

FIG. 4 shows the deflector member 13 in a view from above. The deflector member 13 has an upper surface 13a. The vertical central axis 14 extends centrally through the inlet opening 4a and the upper surface 13a. The upper surface 13a is larger than the cross section area of the inlet opening 4a. The upper surface 13a has a concave shape. The lowest located area of the upper surface 13a is located at the central axis 14. The highest located area of the upper surface 13a is located at a periphery portion in the vicinity of an edge portion 13b of the deflector member 13. The edge portion 13b of the deflector member 13 has a circular shape in a horizontal plane. The upper surface 13a is provided with a plurality of upwardly extending members 13c. The upwardly extending members 13c are arranged on the upper surface 13a along a circular path at equal distances from each other in the vicinity of the periphery edge portion 13b of the deflector 13. Radial flow channels 13d are formed between upwardly extending members 13c through which milk leaves the deflector member 13. The deflector member 13 comprises, at a lower part, a locking member 13e. The locking member 13e is visible in FIG. 2.

Figure 5:
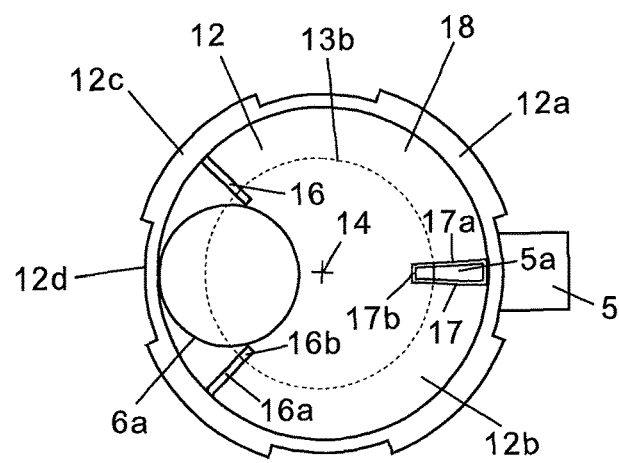

FIG. 5 shows the lower housing member 12 in a view from above. The lower housing member 12 has an inner surface 12b defining a lower part of the inner space of the housing 3. The connection portion 12a comprises a number of radial portions 12c arranged at constant intervals around a periphery portion of the connection portion 12a. The radial portions 12c extend radially outwardly from an outer surface 12d of the lower housing member 12. The lower housing member 12 comprises, at a periphery part, an opening 5a to the first outlet nipple 5. The lower housing member 12 comprises, at a bottom part, an opening 6a to the second outlet nipple 6. The lower housing member 12 comprises three support members 16, 17 configured to support the deflector member 13. The support members 16, 17 are arranged at equal distances from each other in an annular zone located at a radial distance from the vertical center axis 14. The support members 16, 17 have a radial extension in relation to the vertical axis 14. Two of the support members 16 has only the task to support the deflector member 13. The third support member 17 is formed by walls, which, except the task to support the deflector member 13, also defines the opening 5a to the first outlet nipple 5.

Each support member 16, 17 comprises an outer radial part 16a, 17a and an inner radial part 16b, 17b. The outer radial parts 16a, 17a have an upper surface located at a higher level than an upper surface of the inner radial parts 16b, 17b. The inner radial parts 16b, 17b are configured to support a lower surface of the deflector member 13. Each support member 16, 17 comprises a vertical surface connecting the outer radial part 16a, 17a and the inner radial part 16b, 17b. These vertical surfaces of the support members 16, 17 are located at the same radial distance from the vertical center axis 14. This radial distance corresponds to the radius of the deflector member 13. Thus, it is possible to arrange the deflector member 13 on the inner portions of the support members 16b, 17b in a position in which the vertical center axis 14 extends through a central position of the deflector member 13. The vertical surfaces of the support members 16, 17 define the position of the edge portion 13b of the deflector member 13. The position of the edge portion 13b of the deflector member 13 is indicated with dotted lines in FIG. 5.

It is important that none of the upwardly extending members 13c blocks the milk flow from the upper surface 13a of the deflector member to the opening 5a of first outlet nipple 5. Thus, it is necessary to support the deflector member 13 in a specific angular position in which a predetermined one of the flow channels 13d is arranged in a position located immediately radially inwardly of the opening 5a. The downwardly extending locking member 13e of the deflector member 13 is configured to be introduced into a part of the opening 5a defined by the inner radial part of the support member 17b. When the locking member 13e has been introduced in the opening 5a, the deflector member 13 is in an angular position in which one of the flow channels 13d is located immediately radially inwardly of the opening 5a such that this predetermined flow channel 13d provides a reliable milk flow to the opening 5a and the outlet nipple 5. The upwardly extending members 13c are designed such that they form radial flow channels 13d having substantially the same width as the width of the opening 5a.

When the deflector member 13 is in a mounted state on the support members 16, 17, an annular flow passage 18 for the milk is formed between the periphery edge portion 13b of the deflector 13 and an inner surface 11b, 12b of the housing members 11, 12. The object of the deflector member 13 is to receive the milk from the inlet opening 4a and distribute it radially outwardly in a substantially uniform manner to the annular flow passage 18. The opening 5a of the first outlet nipple 5 constitutes a part of this annular flow passage 18. The opening 5a may be dimensioned such that it occupies an angle of approximately 10 degrees of the annular flow passage 18. In this case, the first outlet nipple will deliver about 2-3% of the milk flow through the annular flow passage 18 to the milk sample container 8.

The value of the milk flow in the milk tube 2 varies during a milking process of an animal. The percentage of the substances in the milk is not constant but varies during a milking process of an animal. Thus, in order to achieve a representative milk sample of the composition of the whole quantity of milk from a milking process, it is important that the milk sampling device 1 discharges the same percentage of the milk to the milk sample container 8 at all possible values of the milk flows. It has been verified by experiment that deflector members 13 without upwardly extending members 13c distribute a higher percentage of the milk to the milk sample at high milk flows than at low milk flows.

The milk entering the housing 3 hits the accumulated milk on the upper surface 13a of the deflector member 13. Thereby, the accumulated milk will be pressed radially outwardly on the upper surface 13a. However, the existence of the upwardly extending members 13c reduce the flow area of the milk in the vicinity of the periphery of the upper surface 13a. The reduced flow area, leads to a raised milk level in at least the flow channels 13d between the upright standing members. Consequently, the milk will leave the upper surface 13a of the deflector member 13 in the form of a predetermined number of milk streams arranged at constant distances from each other around the whole periphery of the upper surface 13a of the deflector member 13. With such controlled milk streams from the deflector member 13 to the flow passage 18, it is possible to discharge a substantially equal percentage of the milk to the sampling passage at variable milk flows during a milking process of an animal. Furthermore, it is possible to produce a substantially uniform milk flow through all flow channels 13d even when the peripheral portion of the upper surface 13a of the deflector member 13 is arranged in a somewhat inclined position. Consequently, the milk sampling device does not need to be mounted in a completely accurate mounting position. Furthermore, the upwardly extending members 13c prevent that the milk splashes out from the upper surface of the deflector member 13 at high milk flows. The deflector member 13 receives and accumulates temporarily substantially all milk on the upper surface 13a even during high milk flows.

The milk sampling device 1 comprises no more than three components, namely an upper housing member 11, a lower housing member 12 and a deflector member 13. The assembly process of the milking sampling device 1 comprises the step of mounting the deflector member 13 on the support members 16, 17 of the lower housing member 12 at the same time as the locking member 13e is inserted into the opening 5a defined by the inner radial part of the support member 17b. Thereby the deflector member 13 will be arranged in a center position of the lower housing member 12 and in a specific angular position in which one of the flow channels 13d provides the milk flow to the opening 5a.

During a following step, the connection portion 11a of the upper housing member 11 is connected to the connection portion 12a of the lower housing member 12. During this step, the connection portions 11a, 12a are moved towards each other in a mutual angular position in which it is possible to move the inwardly directed portions 11a of the upper housing member 11 past the outwardly directed portions 12a of the lower housing member 12. After that, the housing members 11, 12 are turned in relation to each other such that a part of each inwardly directed portions 11a of the upper housing member 11 will be arranged in a position vertical below a part of a respective outwardly directed portion 11a of the upper housing member 11. One of the housing members 11, 12 may comprise a stop surface defining the turning position in which the housing members 11, 12 are in a connected state. In the connected state, the sealing member 15 of the upper housing member 11 is pressed against a surface of the lower housing member 12. Thereby, leakage of milk between the housing members 11, 12 is prevented.

The invention is not restricted to the described embodiment but may be varied freely within the scope of the claims. It is, for example, possible that the milk sampling device comprises more than one openings 5a through which milk is discharged to the milk sampling passage 5. The deflector member 13 may have a periphery edge portion 13b of an arbitrary shape. Thus, it does not need to be annular. Furthermore, it is possible to arrange the milk sampling device in a substantially arbitrary position of a milk line. The milk sampling device may, for example, be arranged in a downstream position of a milk meter 9. The milk sampling device may be stationary arranged in a milk line or be temporarily arranged in a suitable part of a milk line when a milk sample is to be taken.

The invention claimed is:

1. A milk sampling device comprising;
    a housing (3) forming an inner space, the housing having an inner surface (11a, 12a) and an inlet opening (4a) to the inner space;
    a deflector member (13) provided with an upper surface (13a) with a periphery edge portion (13b), where a flow passage (18) is formed between the periphery edge portion (13b) of the deflector member (13) and the inner surface (11a, 12a) of the housing (3), the deflector member (13) being mounted in the inner space of the housing (3) in a position below the inlet opening (4a), the deflector member (13) being configured to receive and temporarily accumulate milk entering the housing (3) through the inlet opening (4a); and
    a milk sampling passage (5) with at least one opening (5a) which constitutes a part of the flow passage (18),
    wherein a plurality of upwardly extending members (13c) are arranged on the upper surface (13a) of the deflector member (13) at a distance from each other in a vicinity of the periphery edge portion (13b) of the deflector member (13) such that flow channels (13d) are formed between adjacent ones of the upwardly extending members (13c) along the periphery edge portion (13b) of the deflector member (13), and
    wherein the deflector member (13) is configured to temporarily accumulate milk entering the housing through the inlet opening (4a) and distribute the milk through the flow channels into the flow passage (18), and from the flow passage (18) into the at least one opening (5a) of the milk sampling passage (5).

2. The milk sampling device according to claim 1, wherein said upwardly extending members (13c) are arranged at equal distances from each other.

3. The milk sampling device according to claim 1, wherein the number of upwardly extending members (13c) are in the range of 10-20.

4. The milk sampling device according to claim 1, wherein the upwardly extending members (13c) have a height in the range of 3-10 mm.

5. The milk sampling device according to claim 1, wherein the upper surface (13a) of the deflector member (13) has a concave shape facing the inlet opening (4a) of the housing (3).

6. The milk sampling device according to claim 1, wherein,
    the housing further comprises milk outlet (6), and
    the at least one opening (5a) of the milk sampling passage (5) occupies an area in the range of 1-5 percent of a total area of the flow passage, and 1-5 percent of the milk in the flow passage is discharged via the at least one opening (5a) to the milk sampling passage and a remainder of the milk not discharged via the at least one opening (5a) to the milk sampling passage is discharged via the milk outlet (6).

7. The milk sampling device according to claim 1, wherein the upper surface (13a) of the deflector member (13) is larger than a cross section area of the inlet opening (4a).

8. The milk sampling device according to claim 1, wherein the deflector member (13) is arranged in a position in relation to the inlet opening (4a) such that a vertical axis (14) extends both through a center position of the inlet opening (4a) and a center position of the upper surface (13a) of the deflector member (13).

9. The milk sampling device according to claim 1, further comprising at least one support member (16, 17) configured to support the deflector member (13) in said position below the inlet opening (4a).

10. The milk sampling device according to claim 1, further comprising a locking member (13e) configured to lock the deflector member (13) in a specific angular position in which the deflector member delivers milk to the at least one opening (5a) via only one flow channel (13d) located between two adjacent upwardly extending members (13c).

11. The milk sampling device according to claim 9, wherein at least one of the support members (17) also defines the at least one opening (5a) of the milk sampling passage (5).

12. The milk sampling device according to claim 1, wherein the housing (3) further comprises an upper housing member (11) and a lower housing member (12).

13. The milk sampling device according to claim 12, wherein the upper housing member (11) comprises a first connection portion (11a) and the lower housing member (12) comprises a second connection portion (12a) by which the housing members (11, 12) are releasably connectable to each other.

14. The milk sampling device according to claim 13, wherein the upper housing member (11) comprises an inlet nipple (4) to be connected to a milk tube (2).

15. The milk sampling device according to claim 14, wherein the lower housing member (12) comprises an outlet nipple (5) through which milk is conducted to a milk sampling container (8).

16. The milk sampling device according to claim 14, wherein the lower housing member (12) comprises an outlet nipple (6) through which milk is conducted to a milk meter (9).

17. The milk sampling device according to claim 13, wherein at least one of the lower and upper housing members (11, 12) comprises a sealing member (15) that provides a sealed connection between the lower and upper housing members (11, 12) in a connected state.

18. The milk sampling device according to claim 12, wherein,
the milk sampling passage (5) is an integral part of the lower housing member (12), and
the milk sampling device comprises no more than three separate components, namely, the upper housing member (11), the lower housing member (12), and the deflector member (13).

19. The milk sampling device according to claim 1, wherein,
wherein the upper surface (13a) of the deflector member (13) has a concave shape facing the inlet opening (4a) of the housing (3), the upper surface (13a) of the deflector member (13) having a bowl shape with the peripheral edge portion of the upper surface being at a highest located area of the upper surface (13a) of the deflector member (13),
the housing further comprises milk outlet (6), and
the at least one opening (5a) of the milk sampling passage (5) occupies an area in the range of 1-5 percent of a total area of the flow passage, and 1-5 percent of the milk in the flow passage is discharged via the at least one opening (5a) to the milk sampling passage (5) and a remainder of the milk not discharged via the at least one opening (5a) to the milk sampling passage is discharged via the milk outlet (6).

20. The milk sampling device according to claim 1, wherein,
wherein the upper surface (13a) of the deflector member (13) has a concave shape facing the inlet opening (4a) of the housing (3), the upper surface (13a) of the deflector member (13) having a bowl shape with the peripheral edge portion of the upper surface being at a highest located area of the upper surface (13a) of the deflector member (13),
the housing further comprises milk outlet (6),
the deflector member (13) comprises, at a lower part thereof, a downwardly extending locking member (13e) that extends into a part of the at least one opening (5a) which constitutes a part of the flow passage (18), the locking member (13e) locking the deflector member (13) in a specific angular position in which the deflector member delivers milk to the at least one opening (5a) via only one flow channel (13d) located between two adjacent ones of the upwardly extending members (13c), and
the milk from the one flow channel (13d) is delivered to the at least one opening (5a) and discharged via the opening (5a) to the milk sampling passage (5) and a remainder of the milk not discharged via the at least one opening (5a) to the milk sampling passage is discharged via the milk outlet (6).

21. The milk sampling device according to claim 1, wherein,
wherein said upwardly extending members (13c) have a length measured along the periphery edge portion (13b) of the deflector member (13) and a width measured inwardly across a width of the deflector member (13) from the periphery edge portion (13b) of the deflector member (13) to a center of the deflector member (13), and
the length of each upwardly extending member (13c) is greater than the width of each upwardly extending member (13c), the upwardly extending members (13c) being spaced apart from each other both along the periphery edge portion (13b) of the deflector member (13) and across the width of the deflector member (13), thereby the milk accumulated in the deflector member (13) is distributed radially outwardly through the flow channels into the flow passage (18).

* * * * *